US010451605B2

(12) United States Patent
Hietaniemi

(10) Patent No.: US 10,451,605 B2
(45) Date of Patent: Oct. 22, 2019

(54) DEVICE AND METHOD FOR CHARACTERIZING SOLID MATTER PRESENT IN LIQUIDS

(75) Inventor: Matti Hietaniemi, Espoo (FI)

(73) Assignee: KEMIRA OYJ, Helsinki (FI)

( * ) Notice: Subject to any disclaimer, the term of this patent is extended or adjusted under 35 U.S.C. 154(b) by 432 days.

(21) Appl. No.: 14/342,224

(22) PCT Filed: Sep. 3, 2012

(86) PCT No.: PCT/FI2012/050850
§ 371 (c)(1),
(2), (4) Date: Jun. 5, 2014

(87) PCT Pub. No.: WO2013/030462
PCT Pub. Date: Mar. 7, 2013

(65) Prior Publication Data
US 2014/0293040 A1 Oct. 2, 2014

Related U.S. Application Data

(60) Provisional application No. 61/530,403, filed on Sep. 2, 2011.

(51) Int. Cl.
*G01N 15/04* (2006.01)
*G01N 33/34* (2006.01)
(Continued)

(52) U.S. Cl.
CPC .......... *G01N 33/343* (2013.01); *G01N 15/04* (2013.01); *G01N 21/85* (2013.01); *G06T 7/0004* (2013.01);
(Continued)

(58) Field of Classification Search
CPC .... G01N 33/343; G01N 15/04; G06T 7/0004; G06T 2207/10004; G06T 2207/30124
(Continued)

(56) References Cited

U.S. PATENT DOCUMENTS

2009/0141963 A1* 6/2009 Laurint .................. D21C 5/02
382/141
2011/0073263 A1 3/2011 Shevchenko et al.
2012/0258547 A1* 10/2012 Von Drasek ....... G01N 21/6486
436/172

FOREIGN PATENT DOCUMENTS

WO WO 2008/144383 A1 11/2008
WO WO 2011/072396 A1 6/2011
(Continued)

OTHER PUBLICATIONS

International Search Report issued in PCT/FI2012/050850 dated Dec. 6, 2012.

*Primary Examiner* — William C Vaughn, Jr.
*Assistant Examiner* — Joseph Daniel A Towe
(74) *Attorney, Agent, or Firm* — Birch, Stewart, Kolasch & Birch, LLP

(57) ABSTRACT

The present invention relates to a device, system and method to measure tackiness of a substance, such as pulp, with an on-line or an in-line sensor having a transparent plate with a surface where tacky particles can attach. Attached particles are identified by a camera behind the plate. The camera is focused to detect stationary particles attached to the surface. Measurement is performed directly from a process stream or from a sidesteam and the plate does not need to be removed from the process for the measurement. The plate material may be plastic, such as polycarbonate or acrylic. Additionally, the flow speed may be kept be low, e.g. <0.1 m/s at the measurement position, and/or there may be a stagnation point of flow at or near measurement where the flow speed approaches zero.

32 Claims, 7 Drawing Sheets

(51) Int. Cl.
  *G06T 7/00* (2017.01)
  *G01N 21/85* (2006.01)
(52) U.S. Cl.
  CPC ............... *G06T 2207/10004* (2013.01); *G06T 2207/30124* (2013.01)
(58) Field of Classification Search
  USPC .......................................................... 348/88
  See application file for complete search history.

(56) References Cited

FOREIGN PATENT DOCUMENTS

| | | | | |
|---|---|---|---|---|
| WO | WO 2011072396 A1 * | 6/2011 | ............. | G01N 21/85 |
| WO | WO-2011072396 A1 * | 6/2011 | ............. | G01N 21/85 |

* cited by examiner

DEVICE AND METHOD FOR CHARACTERIZING SOLID MATTER PRESENT IN LIQUIDS

CROSS REFERENCE TO RELATED APPLICATIONS

This application is the National phase of PCT/FI2012/050850 filed on Sep. 3, 2012, which claims priority under 35 U.S.C. 119(e) to U.S. Provisional Application No. 61/530,403 filed on Sep. 2, 2011, all of which are hereby expressly incorporated by reference into the present application.

FIELD OF INVENTION

The present invention relates to a method and device for measuring depositability, e.g. tendency to deposit on surfaces, of solid matter present in liquids. The method and device are particularly well suited for measuring depositability of particulate contaminants of aqueous fluids containing solid matter, such as pulp fibers. The method and device may be realized, for example, in an on-line arrangement, e.g. from a side stream of substance feed or as an in-line measurement from a main substance stream.

BACKGROUND OF THE INVENTION

Often, it is important to know the tendency of solid matter present in a liquid containing solid matter to form deposits on surfaces. This can also be considered as the depositability of a substance, e.g. relative tendency of the solid matter in a substance to form deposits on surfaces. Additionally, this is sometimes discussed as tackiness or stickiness or depositability of a substance. This is particularly important within the paper production industry as well as certain other chemical manufacturing processes or systems containing liquids with solid matter, e.g. cooling waters. Particularly, it is often important to know or estimate depositability of the solid matter or solid contaminants present in a liquid, in particular in an aqueous substance. This is the case in a paper or board making processes. The depositability of the solid matter can be characterized, e.g. by the number of depositing particles on a surface during a measurement, size of depositing particles, number of depositing particles in certain size groups, an area of a measurement surface covered by depositing particles or any combination thereof. The depositing particles are often of hydrophobic nature.

Stickies are various adhesives which enter the paper making process with recycled fibers. These may be, for example; hot melts, pressure sensitive adhesives, envelope glues, contact glues, paper coating adhesives and/or printing ink binders. Stickies are formed or originate from recycled paper or board. Typical compositions of stickies are or include, for instance; acrylates, polyvinyl acetates and/or latexes or any polymeric material in recycled fiber. Additionally, wood pitch originating from mechanical or chemical pulp can cause tackiness. Stickies are tacky on paper machine fabrics, foils, cylinders and calendaring rolls. They can be responsible for significant production losses in the form of cleaning shut downs and web breaks. In other industrial water streams containing depositable, often hydrophobic, solid matter, may also cause problems in the processes.

A significant portion of the stickies in a substance can be removed mechanically in the recycled fiber processing in deinking plants or in OCC (old corrugated containers) plants. Any remaining stickies can be controlled by chemical means. For example, surfaces of sticky particles can be passivated with a chemical that makes them less tacky. Sticky particles can also be kept small in size with dispersing chemicals or they can be fixed to fiber surfaces with fixative or retention chemicals. It is therefore important to know how tacky a pulp is in order to control, manually and/or automatically, the processes and chemical additions for reducing or mitigating stickies, including selection of chemicals.

The depositing tendency of the stickies is often estimated by describing the tackiness of such substances. Existing methods for determining the tackiness of such substances or particulate material, which include plate tests and aeration tests, require samples to be taken from the production process.

There are several standardized macro stickies measurement methods: TAPPI method T277 (TAPPI 1999), INGEDE (International Association of the Deinking Industry) method no. 4, and a method by the International Organization for Standardization (ISO) based on screening and either visual inspection (ISO 15360-1:2000) or image analysis (ISO 15360-2:2001). These or slightly different methods are widely used in the industry and research.

Most laboratory methods that measure the amount of macro stickies are based on either handsheet making or screening of the pulp through 100 or 150 µm slots. These pre-treatments are followed by dyeing the stickies, the background, or both to have a greater contrast between the background and stickies. The stickies are then quantified as area ($mm^2$/kg) or in number of stickies per kg of dry pulp. Though there may be a good correlation between the macro stickies analyzed by image analysis and screen rejects analyzed with DCM extraction and quantification of stickies with FTIR, macro stickies measurement do not always correlate with the deposit problem on paper machines.

Substantial limitations exist in current methods for determining depositing tendency on surfaces of a solid matter present in liquids. For instance, none of the existing methods allow for continuous determination of the depositability of the solid matter as it flows through a production process. Therefore, there exists a need for a method or device which is capable of determining depositability of the solid matter in a continuous manner, in particular on-line.

A further limitation of current methods for determining depositability of the particulate solid matter present in a liquid is that the process stream to be measured continuously or on-line, has to be fractionated before the measurement. That is, the particulate contaminants to be analyzed have to be separated from the sample before the measurement.

Another limitation of current methods for assessing depositability of a substance is the necessity to remove a sample from the production process. The process of removing a sample, or in the case of a plate test to remove a plate which has been exposed to the substance, and transporting the sample to a remote testing location uses both resources and time to determine tackiness. Not only is this generally inefficient but it can also mean that during the elapsed time between sampling and testing an undesired amount of flawed substance is allowed to pass through the sample site.

One or more of the above-mentioned limitations are seen in currently available measurement devices and methods for measuring depositability of particulate contaminants present in pulp and papermaking systems.

Different production processes and substances require differing degrees of accuracy and timeliness with regards to determining the tackiness or depositability of the substance. Therefore, there exists a need for a device or sensor capable of determining the depositability of a fluid substance quickly and without removing a measurement plate for remote analysis.

SUMMARY OF THE INVENTION

It is an object of the present invention to provide a method and device capable of determining a depositability characteristic of solid matter present in liquid, in particular in aqueous substances.

It is an object of certain embodiments of the present invention to provide a method and device for on-line depositability measurement of the solid matter present in liquid, in particular in aqueous substance, in particular in a process flow or a portion of a process flow.

It is an object of certain embodiments of the present invention to provide a method and device for an in-line depositability measurement of an aqueous substance containing solid matter.

The determination of the depositing characteristic of a substance is based upon measurements of depositions on a surface from at least a volume portion of the substance. Depositions, such as, for example, particles, fibers or stickies, which are present on a deposition surface and capable of being captured by an imagery device during measurement, provide a basis for determining the depositing characteristic of the solid matter.

The object of the present invention is achieved by virtue of a novel device for determining depositability of solid matter as defined by the appended device claims, a system for determining depositability of solid matter as defined by the appended system claims, a method for measuring the depositability of solid matter present in a fluid substance as defined by the appended method claims, or by virtue of use of the device according to any of the appended device claim, the system according to any of the appended system claims, or the method according to any of the appended method claims for controlling chemical dosage into a process.

Certain embodiments of the present invention are particularly well suited for measuring depositing characteristic of substances in the pulp and paper making systems. Such substances include, for example: pulps, pulp slurries, water suspensions of fibers and/or particles, process water, white water, etc. As an example, certain embodiments are used in determining a characteristic value of mixed office waste, old newsprint and/or old magazines based de-inked pulp. Other recycled fiber grades such as old corrugated containers or mixed waste type of pulps are also well suited for such determinations. Certain embodiments are also suitable for determining depositability of pitch originating from mechanical or chemical pulp or other types of pulps.

When determining depositability of a desired substance, the original substance may first be diluted, for example by adding an appropriate amount of fluid or secondary substance, and the altered substance then passed through the measurement device. The measurement or features based on the measurement of the altered substance can be used directly for determining depositability of the original substance or it may be used in combination with known qualities of the diluting substance to form a depositability value for the original substance. Similarly, the original substance, or a portion of the original substance, may be concentrated prior to measurement. The substance, original or diluted, may also partly contain air, such as gas.

Water content of the measured process flow is typically over 90%.

Several embodiments are described herein as a device which comprises a chamber arranged such that a substance for which depositability is to be determined for can pass through. Substance is meant generally as a sample entering the measurement chamber, the sample often comprising liquid, in particular aqueous fluid, and solid matter. One will appreciate the varieties of appropriate types of substances from the detailed description below. The solid matter may include solid matter considered as contaminants (e.g. stickies), especially particulate contaminants, and other solid matter (e.g. fibers, mineral pigments). The contaminant solid matter may be partly soluble. However, during the measurement the measured contaminants solid form. The chamber further comprises a transparent portion which at least some of the substance comes in contact with as it passes through the chamber. As the substance comes in contact with the transparent portion particles from the solid matter may, at least temporarily, deposit to the transparent portion. The deposition can be chemical or mechanical. In most cases the deposition is more of chemical nature. An imaging device is then arranged to view the deposited particles on the transparent portion so that depositability of the substance, or sample, can be determined.

The device, system and method according to the invention are particularly suitable for fluid substances containing other solid matter in addition to depositable solid matter. Preferably other solid matter contains fibers.

In certain embodiments, the sensor is arranged as an in-line type sensor with a process stream of a substance, e.g. the entire flow of the substance from the process stream flows through the in-line sensor.

In certain embodiments, the sensor is arranged as an in-line type sensor with a process stream, which can also be considered as an on-line type arrangement with a side stream from a process stream. For example, from a main process stream a sample is taken, either continuously or periodically, and routed through a side stream. A device according to the invention is arranged in the side stream. Said sensor is arranged in-line with the side stream. Side stream goes through the measurement chamber. Side stream is giving flow directly to the sensor, which allows to have continuous on-line measurement of tackiness. In some embodiments the flow through the sensor is controlled to be low at the measurement position. In certain embodiments the flow is arranged so there is a stagnation point of the flow so that the flow speed approaches zero at or near the measurement point. In certain examples, flow speed may be or is arranged to enter the position subject to imaging <0.1 m/s, or more particularly <0.03 m/s.

During imaging period one or more images of deposited particles are captured. Typically image data of an imaging period is analysed with image analysis.

In certain embodiments, the surface may be cleaned with an intermittent shower. The shower flow may be pressurized air, water, cleaning liquid or mixture thereof. Additionally, imaging period may then be between cleaning intervals from between 1 s to 10 hours, more particularly from 10 minutes to 5 hours. In certain embodiments the imaging period may then be between cleaning intervals from between 1 s to 2 hours, more particularly 10 s to 2 hours or more particularly between 1 minute to 30 minutes.

DETAILED DESCRIPTION OF EXEMPLARY EMBODIMENTS

Figure 1A:
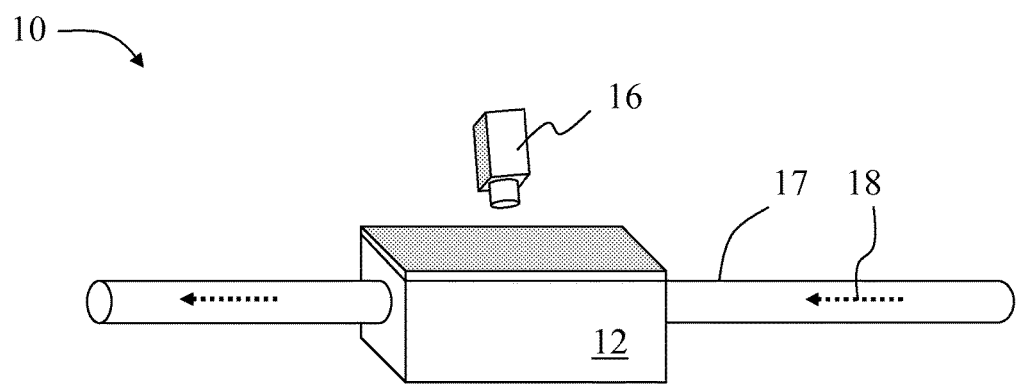
FIG. 1A shows an on-line device, which can be connected to main-stream or to side stream.
Figure 1B:
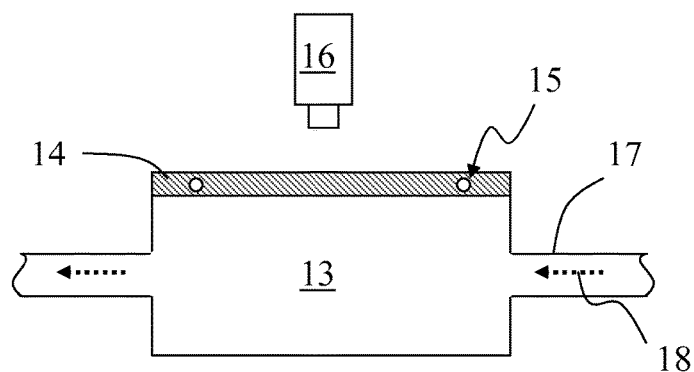
FIG. 1B shows a cutaway of the on-line device of FIG. 1A.

An embodiment 10 of the present invention is shown in FIGS. 1A and 1B. A substance stream 18 is fed through a pipe 17 in to a chamber 12. The chamber 12 in FIG. 1A is shown in an in-line configuration. Pipe 17 can be a main pipe in a production process or it can be a secondary pipe for a side stream of another main stream. The chamber 12 comprises a cavity 13 where the flow passes through. In the figures the cavity is shown as rectangular and larger in cross-sectional area compared to the inlet pipe and outlet pipe 17. The geometry of the chamber 12 and cavity 13 can resemble that of a cuvette, may vary greatly and is not limited to a rectangle. Additionally, the cross section of the chamber 12 and/or cavity 13 can be the same size, roughly the same size or larger than the inlet and outlet pipes. Different geometries can be used based on desired operating conditions. The chamber walls surrounding the cavity may in some embodiments surround only partially the cavity whereby the cavity may be e.g. an open channel.

In the embodiment of FIGS. 1A and 1B the cross sectional area of the flow increases when the substance stream 17 enters the cavity 13 of the chamber from the inlet pipe 18. Thereby the widening of the tube 18 to the larger cross section of chamber 12 provides means for reducing the flow speed of the fluid substance, at least in the vicinity of the imaging area.

At least a portion of the upper portion 14 of the chamber 12 is transparent/translucent and/or substantially unobstructed so that at least a portion of the material flowing through the sensor can be captured by the imaging device 16. The transparent portion of the chamber 12 can be acrylic, polycarbonate, plastic, glass or any other applicable transparent material as described above. Transparent here means that light can enter through the transparent material. The surface of the transparent material exposed to the cavity, i.e. the depositing surface, should be capable of collecting particles for at least a temporary length of time from the substance stream. While the figures show that only the upper portion 14 of the chamber 12 is transparent, any other part of the chamber may be transparent, e.g. sides or bottom thereof, and/or one or more additional portions of the chamber can be made of the same or similar transparent material. Additionally, there may be one or more additional layers/material between the imaging device and the upper portion 14 which should be at least partially transparent/translucent or otherwise not completely obstruct the imaging device during imaging.

In FIGS. 1A and 1B the chamber 12 is shown as a rectangle which has a rectangular cavity 13 and a transparent upper portion 14 which covers the entire upper portion of the cavity. Located above the upper transparent portion 14 is arranged an imaging device 16. The imaging device 16 is arranged such that it is capable of continual or dis-continual focus through the transparent portion onto a, or near a, surface inside chamber, that is, into a surface or to a distance near a surface towards the cavity. The focus area of the camera is adjusted to reach 0-300 µm distance from the transparent surface, preferably 0-150 µm, more preferably 0-30 µm. The imaging device 16 is arranged such that it is capable of continual or dis-continual focus on inner portion of the upper transparent portion 14, that is, on or near the surface of the transparent portion facing the cavity. In order for many imaging devices, such as a camera, to focus through the transparent material, e.g. on an inner surface of a transparent material the material must have a substantial thickness. The necessary thickness of the transparent material 14 is determined based on the imaging device, the specifications of applicable lenses attached to the imaging device and the material of the layer 14. However, the imaging device should be able to continuously and/or dis-continuously monitor any particles that have become deposited to the depositing surface, inner surface of the upper transparent portion 14.

Alternatively, the transparent portion 14 may be provided elsewhere than in the upper region of the device, e.g. lower part of the chamber. Depositing of particles on the surface of the transparent portion is due to other forces that gravitational forces. any.

Imaging device 16 should have a resolution capable of detecting the desired adhered particle sizes which are to be counted. In many applications, e.g. within the paper production industry, a camera having an image resolution of approximately 0.7 µm/pix to 20 µm/pix, preferably 1 . . . 10 µm/pix, preferably 1.5 . . . 5 µm/pix allows detection of particles having sizes over 2 µm which is sufficient in many applications. However, the resolution and selection of the imaging device may vary as necessary.

Having the upper transparent portion 14 of consistent thickness and without curvature aids in the imaging of the particles deposited to the inner surface of the transparent portion 14. Inner surface of the transparent portion is facing the cavity. For this reason a flat, rectangular piece of transparent material having a constant thickness and arranged substantially perpendicular to the imaging device works well in many situations. Similarly, having the depositing surface of transparent portion 14 being a constant distance to the imaging device 16 can be advantageous in certain situations. Additionally, though the transparent portion 14 is shown as covering the entire upper portion of the cavity 13, there only needs to be enough of a transparent portion 14 so that adequate imaging can be acquired. Therefore, only a portion of the surface of the chamber facing the imaging device need be transparent, for example in a window arrangement. Other geometries and arrangements can be implemented without departing from the scope of the present invention.

There may be arranged one or more lighting devices within, on and/or around the chamber to aid with imaging. In FIG. 1B is shown two Light Emitting Diodes (LEDs) 15 arranged within the transparent layer 14. One or more LEDs arranged within the transparent material work well at illuminating the entire piece of material so that an image of the interior surface can easily be obtained. LEDs may also be arranged on the outer or inner surfaces of the transparent material 14. Other lighting sources, such as traditional incandescent bulbs, halogen lights, organic LEDs, lasers and other known lighting sources can be used as applicable to obtain desired lighting for the imaging device. Lighting can be continuous or intermittent.

Furthermore, one or more additional surfaces of the chamber can be made partially or entirely of transparent or semi-transparent material. Such surfaces may contain lighting elements and/or may allow light through in order to provide light for the imaging device. For example, the surface opposite from the imaging device and transparent surface 14 may be transparent and allow light through to effectively back light the particles adhered to transparent surface 14.

Figure 2A:
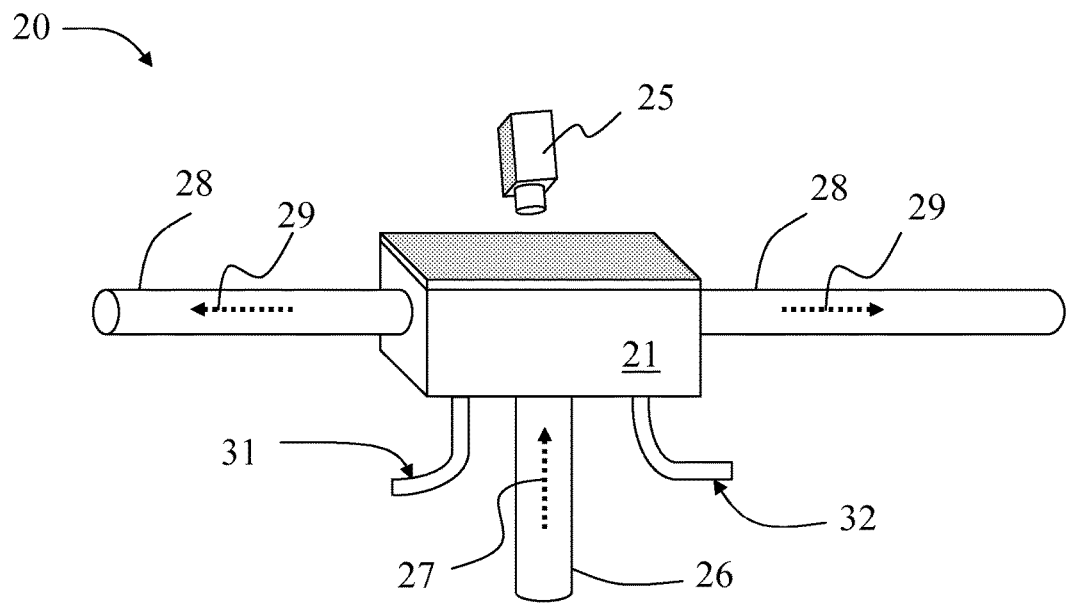
FIG. 2A shows a T-shaped flow-through device.
Figure 2B:
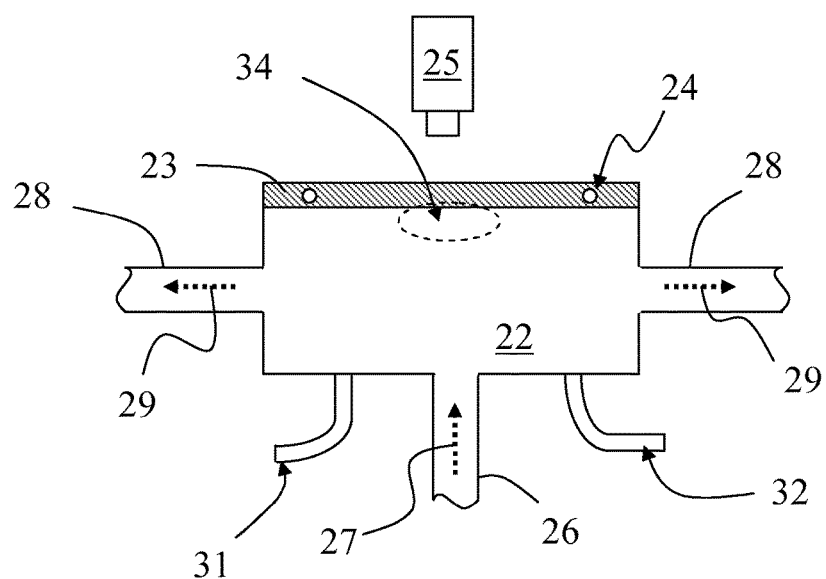
FIG. 2B shows a cutaway of the device of FIG. 2A.

FIGS. 2A and 2B show a "T" shaped embodiment 20 of the present invention. A substance feed 27 travels through conduit 26 in to chamber 21 and exits chamber 21 as feeds 29 through conduits 28 on either side of the chamber. Similarly to embodiment 10, chamber 21 comprises a cavity 22 having a transparent portion 23. Beyond the upper transparent portion 23 is arranged an imaging device 25 which is capable of capturing an image of particles deposited on the depositing surface, e.g. inner surface exposed to the cavity 22, of the transparent portion 23.

In embodiment 20, the transparent portion 23 is arranged opposite from the substance feed inlet 26. Based on this arrangement, when the substance feed 27 enters cavity 22 and is forced out through the left and right conduits 28, there forms a zone 34 at which point the flow is, or nearly approximates, a stagnation zone having, at least temporarily, a feed flow rate at or near 0 m/s. The imaging device 25 is arranged to view at least a portion, and often the greater portion or all of the surface of the transparent portion 23 around the stagnation zone 34. Similarly to embodiment 10, there can be one or more lighting elements 24.

In the embodiment of FIGS. 2A and 2B the flow 27 entering the cavity 22 through inlet pipe 26 is divided into two outlet flows 29. The division of flow to two outlet flows may allow reducing the flow speed of the fluid substance within the cavity of the chamber, at least in the vicinity of the imaging area.

In the embodiment of FIGS. 2A and 2B the cross sectional area of the flow increases when the substance stream 27 enters the cavity 22 of the chamber 21 from the inlet pipe 26. Thereby the widening of the tube 26 to the larger cross section of cavity 22 provides means for reducing the flow speed of the fluid substance in the cavity, at least in the vicinity of the imaging area.

In the inlet to the cavity or outlet from the chamber the flow speed may exceed the flow speed occurring at the imaging area. In certain embodiments typical flow speeds at the inlet or outlet are less than 0.5 m/s.

Due to the formation of the stagnation zone 34 in the T shaped embodiment 20, it is often necessary to flush the chamber in order to remove time to time deposited particles. Chamber 22 in the present embodiment is therefore fitted with a flush fluid line 31 and a flush air line 32. When the chamber, or at least the depositing surface is to be flushed the substance flow is restricted and a combination of air, e.g. pressurized air, and fluid, e.g. water from the paper production process, is used from lines 31 and 32 to flush the chamber. The flushed substance can then be removed from the chamber through conduits 28 or feed 27 or by a dedicated flush conduit (not shown).

Although there is shown separate fluid and air lines 31 and 32 to flush the system, alternative elements may be used to flush the chamber. For example, a single line can feed both a fluid and a gas or only a single substance capable of flushing the chamber. The fluid can be water, chemically treated water, a chemical substance, or virtually any known substance capable of flushing the chamber. Other methods of cleaning the inner surface of transparent layer 23, for example a mechanical means such as a squeegee, may be used in conjunction with, or in place of flushing. The cleaning can therefore be performed both with or without the presence of the substance flow 27.

While embodiment 20 is shown as a "T" arrangement having inlet and outlet conduits at right angles, the entry angle of the feed inlet 26 and/or the exit angle of feed outlets 28 may be other than right angles. Furthermore, there may be one, or more than two feed outlets. Outlet can be arranged to occupy continuously 360 degrees around the imaging area by arranging another chamber to collect outlet flow. The geometry and characteristics of the chamber and cavity can vary as discussed with regards to embodiment 10 above.

Figure 3:
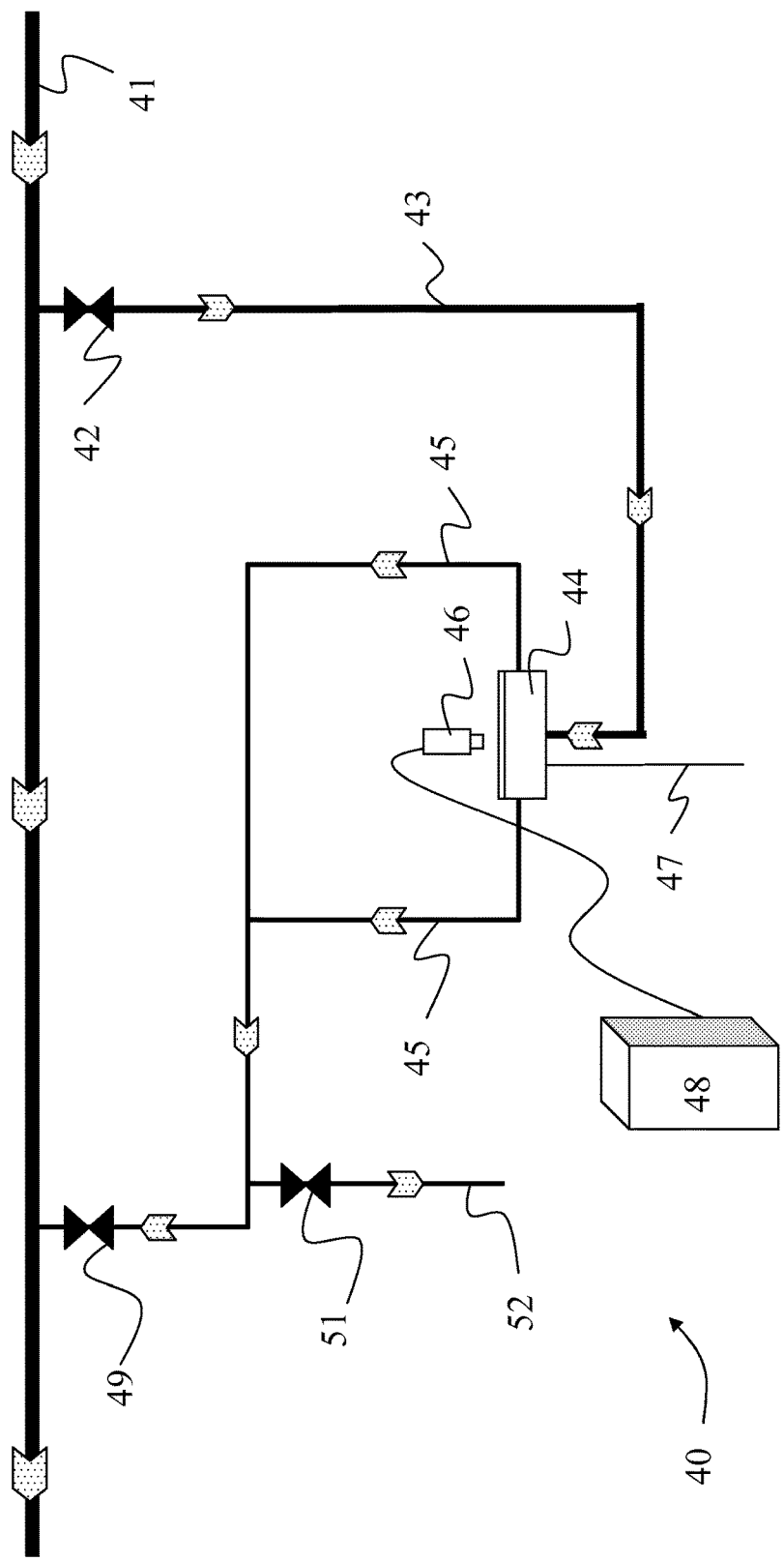
FIG. 3 shows an embodiment of a device within a process stream.

FIG. 3 shows an embodiment 40 of a system utilizing a device in an online, side stream, arrangement. A main substance feed line 41 has a side stream line 43 which is controlled by a regulating means 42, e.g. a valve. When the tackiness of the feed substance is to be determined, the regulating means 42 allows at least a portion of the feed substance to be directed through to line 43 for a period of time. The substance feed from line 43 then flows in to a sensor chamber 44 where the depositability of the substance feed is determined. The chamber 44 can be any chamber as described above and is shown in FIG. 3 as a "T" arrangement similar to embodiment 20 of FIGS. 2A and 2B.

Particles from the feed substance adhere or deposit to a transparent portion of chamber 44 and are recorded by imaging device 46. Imaging device 46 is connected to a CPU 48. Images from the imaging device can be continuously or selectively stored in a memory of, or accessible by, CPU 48. CPU 48 contains programming stored on a computer readable medium, such as a hard drive or removable transitory or non-transitory medium, which is capable of analyzing the image data from the imaging device to determine the depositability of the substance feed. CPU 48 can be any known computing medium, such as a PC, MAC, server, cloud server, processing unit, PDA, a portion of the imaging device itself, etc. The imaging device may have resolution which is capable of capturing particles having a size <50 µm, or more specifically <5 µm, or in some cases <150 µm or <100 µm.

The determination of the depositability of a substance is based upon a measurement of depositions from at least a portion or the volume of the substance. In particular, the device and method of the invention allow determination of the depositability without fractionation of the substance or sample. Depositions, such as, for example, hydrophobic particles, stickies, pitch, adhesives originating from coated broke or other particles, which are present on a deposition surface and capable of being captured by an imagery device during measurement, provide a basis for determining the depositing characteristic of the substance.

The determination programming is capable of determining a representative value and/or quality from the captured images. For example, the programming is capable of causing a processor to perform the step of counting the number of particles which are present in the imaging, through any known image recognition processing. For instance, the program can calculate an average from several images or may compare several images to eliminate non-attached particles away from the result. Dirt accumulated to the imaging system can be removed from result data by neglecting particles which were present in the images before a particular measurement is started.

In addition to counting the number of particles, the determination programming may be arranged to determine the size of each particle and/or of particle groups. In addition, the determination programming may be arranged to determine a percentage of the measurement area covered by deposits or certain kind and/or size of deposits. At some point, e.g. prior to determination, the processing can be arranged to determine a predefined or software based gray level and/or reference image from which the captured image or images for measurement are compared. Any of these values, or any combination thereof, can be used standalone or as a basis for the depositability of the sampled substance, altered substance or original substance.

A value characterizing the depositability of a substance can be, for example, the total number of particles, an averaged number of particles, a percentage of a covered surface area, average gray scale of image, colour or a product of an algorithm taking in to account one or more of said example values. Algorithm may also do a classification of particles to identify for instance stickies, ink particles, inorganic deposits, pitch, fibers, pigments, air bubbles and microbiological slime. Classification can be based on e.g. shape, size and color. Values used for characterizing depositability in best way may depend e.g. on the particle size or type in a sample. One of ordinary skill in the art will recognize numerous values and quantities achievable using the devices described herein which do not depart from the scope of the present invention.

The values obtained based on the measurement describing particles analysed from the depositing surface, may be used as such or related e.g. to the total solid content in the substance. When determining a characteristic value of a desired substance, the original substance may first be diluted, for example by adding an appropriate amount of fluid or secondary substance, and the altered substance then passed through the sensing device. The measured quality of the altered substance can be used directly for determining a relative characteristic value of the original substance or it may be used in combination with known qualities of the diluting substance to form a characteristic value for the original substance. Similarly, the original substance, or a portion of the original substance, may be concentrated prior to measurement.

The device can be operated in discontinuous or continuous mode.

When the device is operated in a discontinuous mode, discrete particle counts of images can be achieved and stored allowing the determination programming to assign a discrete depositability value for the substance in the image at the given time. When the sensor is operated in a continuous, or on-line, mode then the change, or relative change, of particles in images over a given period of time can be used to determine a relative depositability of a substance compared to a norm or substance at a previous point in time. This value can be indicative, or used to determine a consistency value for a substance stream feed over one or more periods of time. In an embodiment, particles can be classified by their area, grey scale and/or color. Additionally, the total area covered by deposited particles can be used as a measurement value. Further, average grey scale of the image can be used as a measurement value.

In an embodiment of the continuous mode accumulation rate of the deposited particles can be followed. In an embodiment of the continuous more the deposited particles can be followed without (stops for) flushing or cleaning the sensor or surface thereof. To detect cumulative amount of deposited particles it is important to detect stationary particles. Moving particles can be neglected by taking gray scale or colour scale average pictures from several pictures or detecting only the particles which show up in same place in subsequent pictures. From the pictures which are without moving particles, deposited particles are detected for examples by thresholding or with more advanced image analysis means. Threshold values can be selected depending on the case. Also other particle detection techniques can be used instead. The detected particles are classified and e.g. counted. Accumulation or accumulation rate of the deposits may be followed in any suitable periods, in some embodiments in longer time periods, e.g. from 1 to 24 hours preferably for 2 to 8 hours. Flow inside the sensor is randomly directed which can deposit particles faster onto the surface or can even release particles from the surface. Therefore often longer time periods of follow-up is recommended. To follow accumulation or accumulation rate of deposited particles e.g. the slope of the number of particles or total area of deposited particles can be calculated. These values can be calculated for e.g. total population of the particles or per size classes of the particles.

Substance feed from the chamber exits through one or more outlet conduits 45. In an embodiment similar to embodiment 20, and chamber 44 shown in FIG. 3, there can be a flushing means 47 which is used to flush the chamber and/or clean the imaged surface of the chamber. When operated in a discontinuous mode, the flushing will normally take place when the substance feed flow has ceased. In an embodiment where the flushing means is a fluid and/or gas fed through a line 47 then the flushed substance can exit the chamber through conduit(s) 45 and be diverted to a waste line 52 through a control valve 51. Substance feed which is taken from the main stream 41 through the side loop can either be reintroduced to the main stream through a control valve 49, it can be returned back to any other part of the process and/or it can be discarded through a waste line 52.

A side loop as described with respect to FIG. 3 may contain additional valves, controllers, conduits, one or more pumps, and/or additional sensors. Furthermore, main line 41 may have an additional device according to the present invention. For example, there may be an inline device or sensor, such as described by embodiment 10, prior to control valve 42. If the inline sensor detects a relative change in the tackiness of the substance then a portion of the flow can immediately be diverted to the side loop for more detailed and accurate online analysis.

Sensors or devices and systems and methods as described herein can be particularly useful in the pulp and paper and board production industry. For example, they can be used with testing mixed office waste pulp (MOW), mixed waste (MXW), de-inked pulp (DIP), old newspaper pulp (ONP), old magazine paper pulp (OMG), old corrugated container pulp (OCC), groundwood pulp (GW), thermomechanical pulp (TMP), bleached chemithermomechanical pulp (BCTMP), coated broke and other pulp types or any mixtures containing these. Typical solid content of the substance, e.g. pulp can be 0.3 . . . 12%. This is typical consistency between the pulp storage tower and paper machine. Sometimes the consistency may be even 0.1 to 12%, e.g. in tissue paper machines. This is also suitable operation area for the measurement. For side stream sensor solids content <4% is preferable. The analyzed pulp can be in its original, processed, processing or diluted form. Measurement can be performed also from white water or from filtrate water of stock preparation, pulping, paper making or board making processes. In that case solid content is typically <1%. Preferable measurement point could be paper machine short loop, where deposits easily grow to the larger size.

The measurement devices are also capable of assessing the effect of agents, reagents and other chemicals, for example passivation agents, dispersing agents, surfactants and fixatives, on the depositability of such pulps. Chemical may be used to modify or reduce the amount of same deposits as the device according to invention is measuring. Measurement information can be used to adjust the dosage of the chemical(s) to reach low enough deposition tendency with minimal or optimal chemical consumption. The chemical dosage adjustment can be performed also with control system based on measurement result from the device. The control can be cascaded, feed forward or any other available control logic.

In a system such as described in FIG. 3, a water line (not shown) can add water to the diverted stream line 43 prior to, or at the entrance to chamber 44, to dilute the substance feed to a desired concentration. A consistency measurement device may be added at one or more points within the loop to determine the original and/or adjusted substance feed consistency. In such an embodiment, the diverted and diluted substance feed would most likely not be returned to the main line. Therefore, valve 49 and the associated line connecting the loop back to the main line 41 can be removed.

For example, a MOW DIP having a consistency of 5%, preferably 4.8%, pulp in a main line can be tested as it is or it can be diluted. For instance, in a system as described with respect to FIG. 3, the depositability of the MOW DIP is desired to be discontinuously tested at regular intervals. During a period of 1.5 hours the depositability of the pulp is tested 8 times. At a determined, or predetermined time, control valve 42 is opened to allow pulp from the main line to travel in to the side loop along line 43. The pulp in line 43 may first pass through a sensor which measures its consistency.

The pulp then flows towards chamber 44 and at some point may have water added to it, for example tap water at 50 degrees Celsius, to dilute the feed to 2% consistency. The consistency of the diluted feed may then be measured again before entering chamber 44. The substance then is allowed to flow for a period of time, e.g. a predetermined 5 minutes, to allow tacky material to deposit to an acrylic plate of the chamber 44. After the period of time, imaging is conducted for a second period of time, e.g. a predetermined 2 minutes. The substance can be flowing during the imaging period or it may already have been ceased. After the imaging period is concluded the control valve 42 restricts, or stops completely, flow from the main line 41 in to the side loop if not already done. The substance feed is then either allowed to re-enter the main line 41 or is diverted to a dump line 52.

After the imaging period has expired, the flushing means flushes the chamber and/or cleans the acrylic plate of chamber 44. Data from the imaging period is sent, or having been sent in real time, is stored and/or immediately analyzed by CPU 48. The image is then analyzed to determine e.g. the amount, size and/or size distribution of deposited particles in one or more captured images during the imaging period. When multiple images are taken during the imaging period, particularly while there is flow present during the imaging period, the results from one or more images may be averaged and the averaged data used to determine tackiness.

The chamber may also be open to the main process stream, in such case providing an in-line measurement. One function of the chamber can be to reduce flow speed to a point at which tacky particles or particles having a tendency to deposit on a surface, can attach or deposit, at least for a period of time, to the imaged surface and the remainder of the flow will not wipe the particles off before they are measured. However, especially in cases where flow speed is not an issue, a chamber to slow down the feed may not be necessary. In any event, in place of an actual chamber, a portion of a line, pipe or conduit, such as a main feed line, may contain a transparent portion and be arranged in a manner as described herein. Therefore, the feed inlet would be an imaginary portion of the conduit prior to the transparent portion and the feed outlet would be an imaginary portion of the conduit following the transparent portion. The section of the conduit between said imaginary portions would represent the chamber. As such, the space within said defined chamber would represent the cavity.

Figure 4:
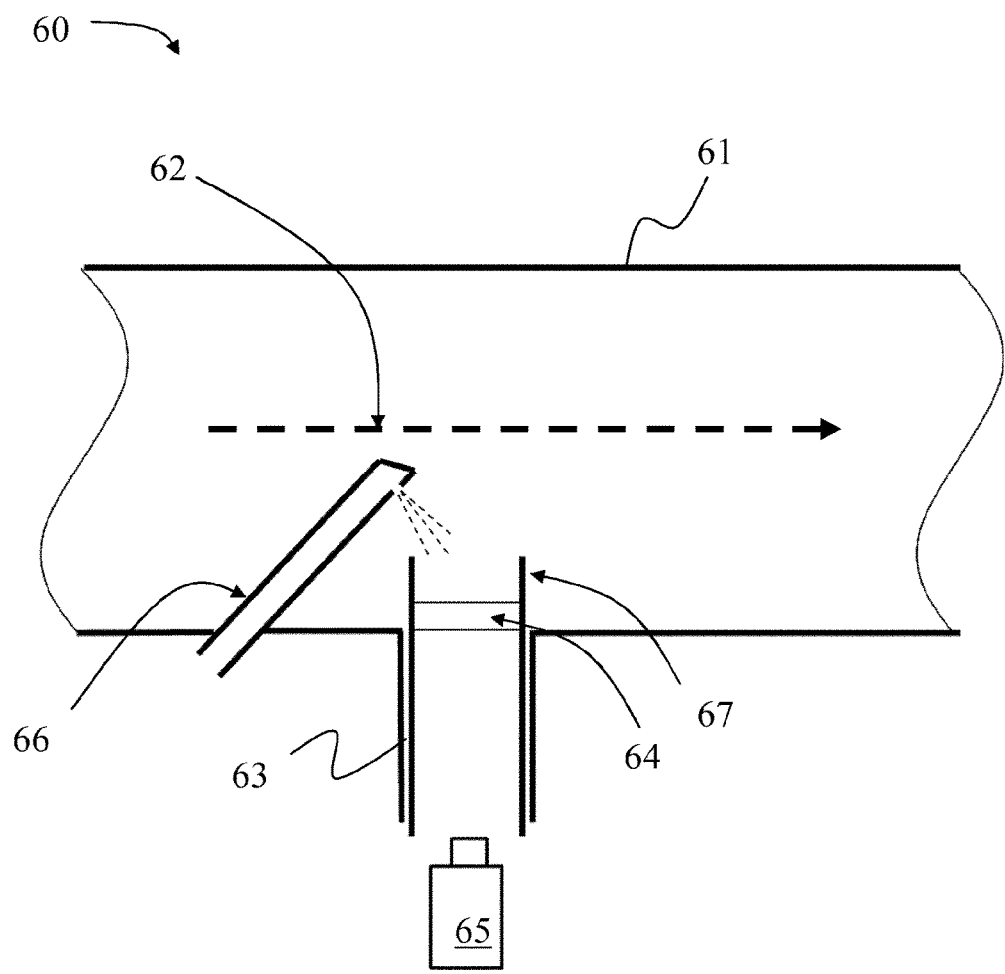
FIG. 4 shows an in-line embodiment located directly within a conduit.

An example of such an embodiment is shown as embodiment 60 in FIG. 4. Conduit 61, which can be for example a main feed line containing a pulp substance, has a generally unrestricted substance flow 62. A portion of the conduit is replaced with a transparent material 64. Imaging device 65 is arranged with respect to the transparent portion 64 as described above.

The transparent portion 64 can form a part of the inner and outer surfaces of the conduit (not shown) such that the conduit is otherwise unmodified. In the example embodiment shown in FIG. 4, there is an insert 63 which protrudes a portion of the way in to the conduit. The insert contains the transparent portion 64. Additionally, the insert can extend slightly past the transparent portion. This extension 67 can be used to create a desirable, and in many cases minimal, disturbance in the substance flow 62 around the transparent portion 64. The extension 67 may also act to slow down locally the flow speed in the conduit. Thus extension 67 may provide means for reducing the flow speed of the fluid substance, at least in the vicinity of the imaging area. This disturbance can facilitate the deposition of particles as well as prevent deposited particles from being washed away by the general flow 62. It is thought that the depositing particles are adhering to the depositing surface. In some cases the particles may deposit mechanically to the surface or near the surface, within the focus of the imaging.

Additionally, a cleaning means 66 is shown in an extended position. The cleaning means 66 may comprise a nozzle which can spray a substance; such as air, water and/or chemical compound, to the exposed surface of the transparent portion to clean the depositing surface of the deposited particles. The cleaning means 66 may be in a fixed position, however, the cleaning means may also retract so that it does not disrupt flow 62 and extend when desired to clean said surface of the transparent portion. Other cleaning means which are capable of cleaning adhered particles from the surface, such as those described with respect to the flushing means, or other means can be utilized.

Figure 5:
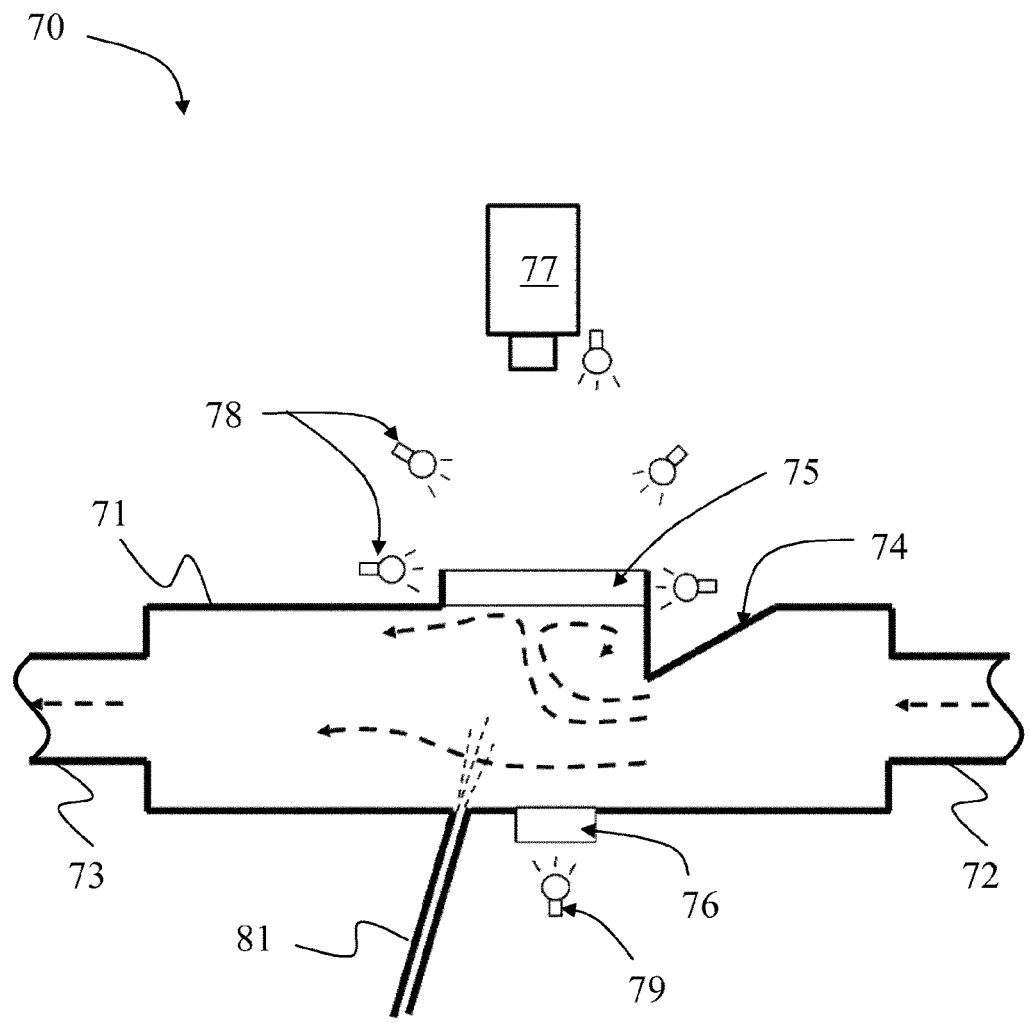
FIG. 5 shows an embodiment of a device with a chamber having an irregular geometry.

FIG. 5 shows a further embodiment 70 of the present invention. A chamber 71 is arranged having an inlet conduit 72 and an outlet conduit 73 in an in-line arrangement similar to embodiment 10. Chamber 71 has a depression 74 which is arranged prior to the transparent portion 75. As is illustrated by the dashed flow lines, the depression causes a disturbance in the flow through the chamber to facilitate particle adhesion and measurement. Instead of a depression any form of contraction may be used. This disturbance may cause an eddying zone at or around the transparent portion. Different arrangements and geometries of depressions and obstructions located within the chamber can be used to this effect. The contraction of the chamber may also create a stagnation point of flow which may accelerate deposition of particles to the surface as after the contraction the cross sectional area of the flow route is increased again.

Imaging device 77 is arranged to capture through the transparent portion the particles deposited to transparent portion 75. The imaging device 77 is arranged to be focused on the imaged device surface (depositing surface) or preferably to a distance of up to 150 μm, preferably up to 100 μm from the depositing surface towards the cavity, in particular between 0 to 50 μm. The imaging device is arranged outside the cavity to capture images through the transparent surface. Additionally, as shown in the figure, several lighting devices 78 are located around the imaging device and outside the transparent portion 75. Furthermore, a secondary transparent portion 76 is located opposite from transparent portion 75 with a lighting source 79 arranged to effectively back light transparent portion 75 and the images captured by imaging device 77. Similar to FIG. 5 there is shown a cleaning means 81 in an unobtrusive, retracted position.

EXAMPLE 1

Mixed office waste based deinked pulp (MOW-DIP) and undeinked recycled pulp containing 50% old newsprint and 50% old magazine paper (ONP-OMG) are used as test pulps. Additionally, MOW-DIP was treated with a common detackifying chemical containing polyvinylalcohol.

The extractives content of the pulps was determined gravimetrically by extracting freeze dried pulp samples with tetrahydrofuran (THF) before the tests. The share of polymeric fraction from total extract was determined by using liquid chromatography with size exclusion column (HPLC-SEC). The result was calculated as mg/g dry pulp.

The measurement arrangement used was a T-shaped cuvette. The cuvette, i.e. the imaging area, was made of an acrylic plastic. Pulp feeding was arranged by circulating recycled fiber pulp through the cuvette having a 2% consistency in a pumping loop with a 50 liter storage vessel. The flow speed at the exit of the cuvette was approximately 0.1 m/s. The cuvette was flushed with water 8 times during a one hour run. After each washing cycle 5 minutes of flow was maintained to allow the tacky material of the pulps to deposit on the acrylic plate. Thereby imaging period was 5 minutes. One image at the end of the imaging period was taken.

The camera for online imaging was installed above the cuvette cover. Imaging was performed 5-8 times for each pulp sample and the transparent plate was cleaned between the repeats. Then the average particle count per image of a trial point was calculated. The pixel resolution was 2 μm/pix and the imaging area was approximately 2 cm×1.5 cm. Furthermore, horizontal illumination was carried out by using LED modules.

TABLE 1

| | MOW-DIP | MOW-DIP with 500 g/t detackyfier | ONP/OMG undeinked |
|---|---|---|---|
| Polymers (stickies), mg/g | 0.60 | 0.55 | 4.7 |
| Total extractives, mg/g | 1.4 | 1.4 | 14.7 |
| Average number of deposited particles/image | 28 | 15 | 52 |

The results above in Table 1 show that by using the imaging method it is possible to assess particulate contaminants of a pulp sample, and of a sample of for which contaminants have not been separated prior to measurement. In addition, it was possible to assess effect of chemistry on the tackiness of the samples. As can clearly be seen between the treated and untreated MOW-DIP, the detackyfier (passivation chemical containing 9% polyvinyl alcohol in aqueous solution) reduces the number of deposited particles as expected. Additionally, the ONP/OMG which had a greater amount of extractives and stickies showed a much greater average number of deposited particles per image. This demonstrates that the imaging method is a quick way to efficiently determine relative depositability of substances.

According to embodiment, a method for measuring the depositability of solid matter present in a fluid substance is provided. The method comprises the steps of; having at least a portion of a substance stream contact a surface of a transparent portion of a chamber facing the cavity of the chamber for a first period of time, said transparent portion of the chamber having an imaging device arranged to capture imagery of particles deposited to the exposed interior surface contacted by the substance stream, capturing one or more images of particles deposited to said surface of the transparent portion of the chamber, analyzing said one or more images to determine a value for said solid matter and/or said fluid substance based at least in part on the captured imagery, said value being a relative or indicative depositability value, the total number of imaged particles, number of depositing particles on a surface during a measurement, an averaged number of particles averaged over a predefined surface area and/or time period/number of images, a percentage of a covered surface area, size of depositing particles, number of depositing particles in certain size groups, an area of a measurement surface covered by depositing particles, grayscale shade and/or color of the imaged particles, or any combination thereof.

According to one embodiment, a device for determining depositability of solid matter is provided. The device comprises a chamber having a cavity, said chamber having at least one transparent portion, and at least one inlet to the chamber for a fluid substance and at least one outlet from the chamber for a fluid substance, and an imaging device arranged to capture imagery of a space within the cavity and/or at least a portion of a surface of the transparent portion of the chamber, said surface being exposed to in the cavity of the chamber.

The examples and embodiments described herein are meant to help illustrate the present invention and are not meant as limiting examples. Numerous variations and combinations of elements from the specific embodiments and examples disclosed herein can be achieved by those of ordinary skill in the art without departing from the scope of the present invention. Furthermore, modifications such as; chamber geometries, construction, arrangements and dimensions, and/or various imaging and/or processing devices and techniques known to those of ordinary skill in the art but not disclosed herein may be made without departing from the scope of the invention.

EXAMPLE 2a

Figure 6:
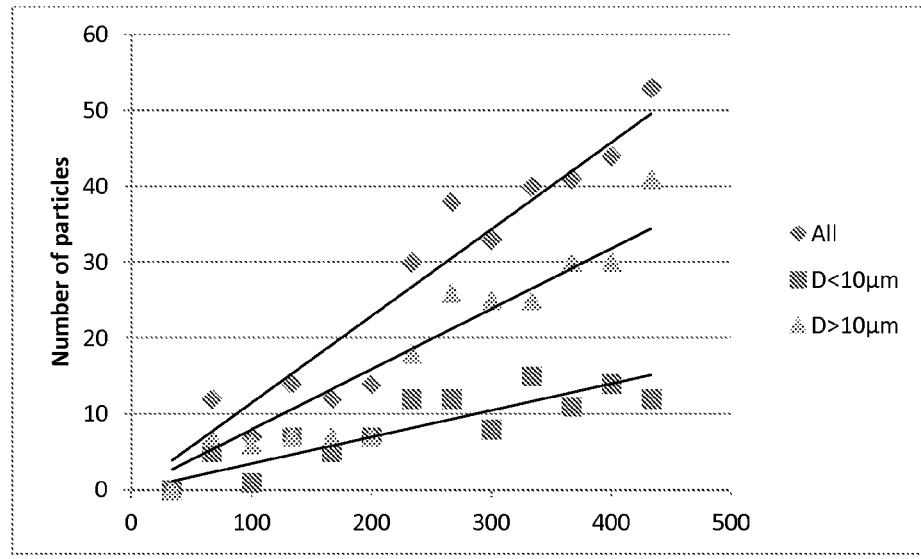
FIG. 6 shows image analysis data from an embodiment. Number of deposited particles as a function of time are shown for two particle size categories when a pulp containing 65% deinked pulp is used.
Figure 7:
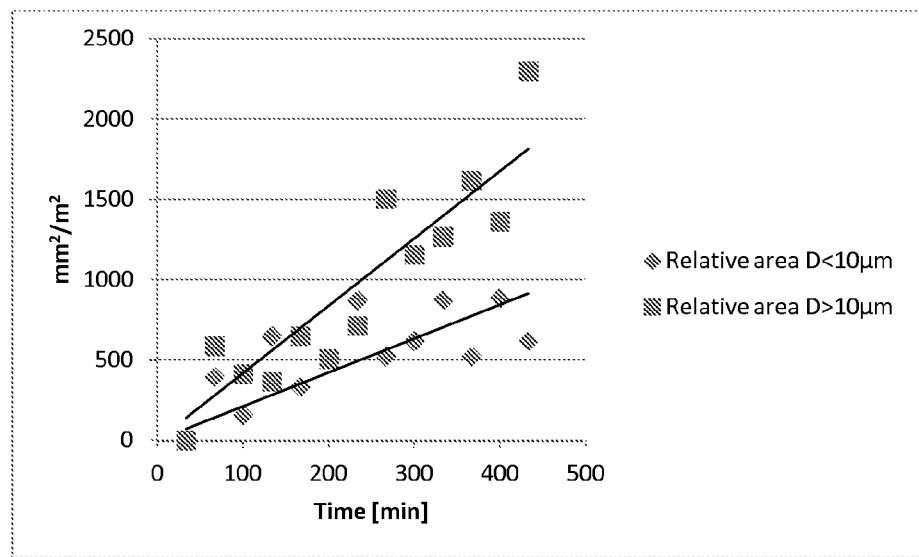
FIG. 7 shows image analysis data from an embodiment. Relative area of deposited particles of the total deposit area as a function of time for two particle size categories when a pulp containing 65% deinked pulp is used.

A pulp mixture containing 65% mixed office waste (containing recycled fiber stickies) based deinked pulp (MOW-DIP) and 35% kraft pulp was used as test pulp (cf. FIGS. 6 and 7). Kraft pulp used was without stickies. Test was performed with production scale tissue paper machine producing toilet paper.

Measurement chamber was a T-shaped cuvette. The cuvette, and thereby the imaging area, was made of an acrylic plastic. Thick stock from the paper machine was directed to a side-flow, diluted and directed continuously through the measurement chamber. The flow speed at the outlet of the chamber was approximately 0.1 m/s.

The camera (1.4 Mpix CCD camera) for online imaging was installed above the cuvette cover. The pixel resolution was 2 µm/pix and the imaging area was approximately 2.9 mm×2.1 mm. LED modules were located around the camera at the same side of the transparent portion as where the camera was located.

The cuvette was not flushed with water during the test. 100 images were taken during 33 minutes whereby time between images was 20 seconds. Thereby imaging period was 33 minutes. From the 100 subsequent images gray scale average image was calculated to remove moving particles from the data. From the average image particles were identified and calculated by computer software. Number of particles per image area and relative area of the deposited particles were calculated and plotted as a function of time. In the calculation of the relative area of particles the particles were assumed to be of circular form. E.g. a slope of a curve for number of all deposits detected or for relative area (0.11 l/min or 6.3 mm$^2$/(m$^2$ min) respectively). Also, e.g. a number or relative area of deposited particles at a selected time moment can be used to estimate depositability of the substance.

The device, system or method according to the invention can be used for controlling chemical dosage into a process, wherein the chemical is capable of modifying the depositability of solid matter present in a fluid substance. The chemical may be in certain embodiments a passivation agent, dispersing agent, surfactant or fixative, or a combination thereof.

Non-limiting examples of fixatives are polyamines, poly-DADMAC, cationic starches and cationic polyacryl amides (PAM) with low intrinsic viscosity (<4 dl/g).

Non-limiting examples of dispersing agents are naftalenesulphonates, maleic acid anhydride copolymers and acrylic acid copolymers.

Non-limiting examples of passivating agents are anionic and non-ionic surfactants, ethoxylated fatty acid alcohols and polyvinyl alcohols.

EXAMPLE 2b

Figure 8:
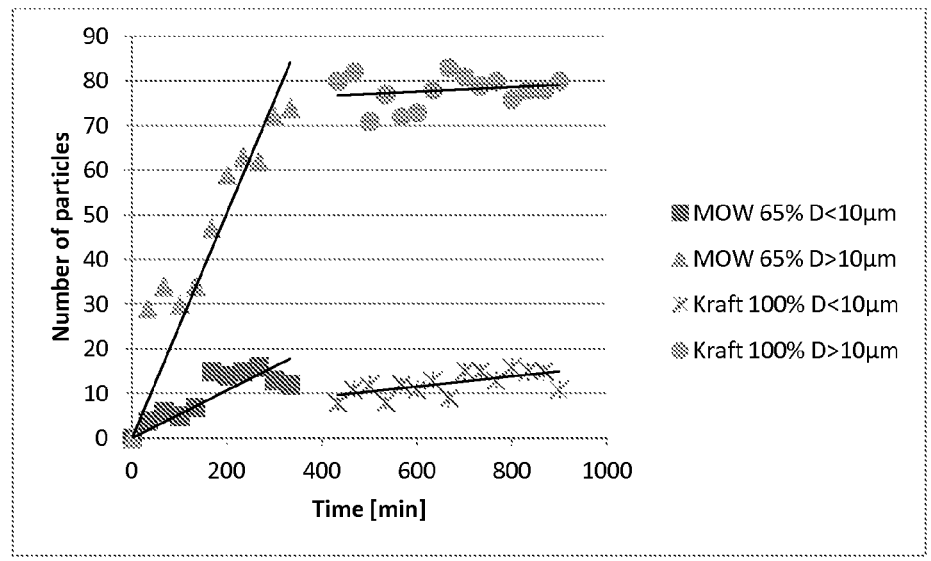
FIG. 8 shows image analysis data from an embodiment. Number of deposited particles as a function of time are shown for two particle size categories when a pulp containing 65% deinked pulp is first used and changed to 100% kraft pulp.
Figure 9:
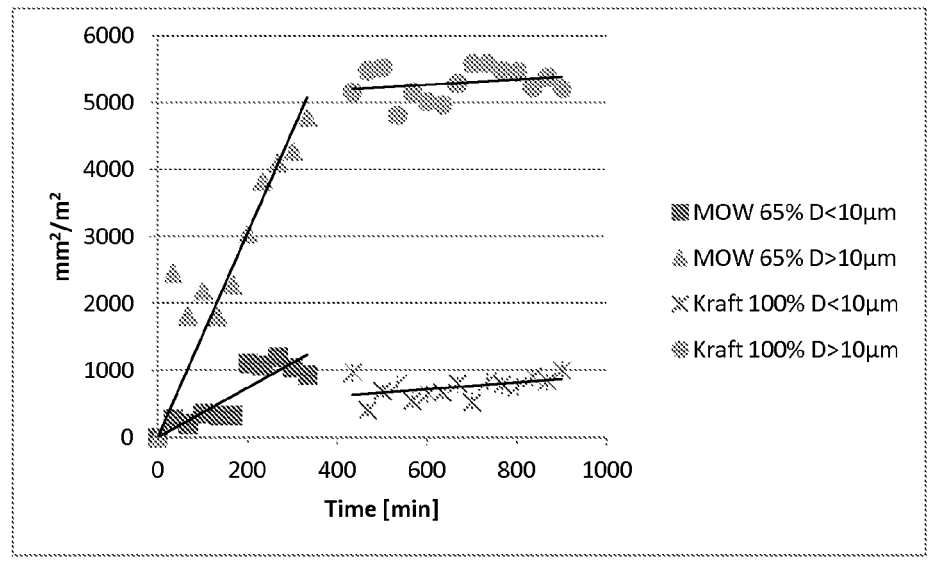
FIG. 9 shows image analysis data from an embodiment. Number of deposited particles as a function of time are shown for two particle size categories when a pulp containing 65% deinked pulp is first used and changed to 100% kraft pulp.

In this experiment (cf. FIGS. 8 and 9) another pulp mixture of MOW-DIP % 65% and 35% kraft pulp was used (MOW 65% in figures). Experimental setup was otherwise similar to Experiment 2a. After about 350 minutes pulp was changed in a 100% kraft pulp whereby the number of imaged deposited particles and relative coverage thereof on the imaging surface remained almost constant. Despite that the kraft pulp is without sticky material, there may still be some stickies present in the circulation water systems and in broke system.

Accumulation rate of the deposited particles is higher with a pulp containing deposited particles. E.g. values at certain time moments or slope of the curve describing number of deposited particles or relative are of deposited particles on the analysed imaging area can be to estimate depositability of the substance. The values or any calculated values can be used as such to compare depositability of the process flows or they can be related to e.g. solid matter of the whole process flow.

A device for determining depositability of solid matter comprising;
 a chamber having a cavity, said chamber having at least one transparent portion,
 at least one inlet to the chamber for a fluid substance and at least one outlet from the chamber for a fluid substance, and
 an imaging device arranged to capture imagery of at least a portion of a surface of the transparent portion of the chamber or of a space in the vicinity thereof, said surface being exposed to the fluid substance in the cavity of the chamber.

Said surface may be cleaned prior to and/or after said second period of time.

The analyzing and determining may be performed by one or more processing units.

Said transparent portion of the chamber may be fixed.

The determining of the number of particles and/or particle area may be performed without the removal of and/or displacement of the transparent portion of the chamber of which images have been captured.

The capturing images may be done without the removal of and/or displacement of the transparent portion of the chamber of which images have been captured.

The invention claimed is:

1. A device for determining a tendency to form deposits of a fluid substance containing solid matter, which is not treated with a dye, the device comprising:
 a chamber having a cavity, said chamber having at least one transparent portion forming a part of the inner and outer surfaces of said chamber,
 at least one inlet to the chamber for a fluid substance and at least one outlet from the chamber for a fluid substance, and
 an imaging device arranged to capture imagery of at least a portion of said inner surface of the transparent portion of the chamber or of a space in the vicinity thereof, when the fluid substance is flowing through the chamber to expose said inner surface to the fluid substance in the cavity of the chamber, wherein said imaging device is adapted to produce image data representative of the tendency to form deposits of the fluid substance containing solid matter particles that stick to said inner surface of the transparent portion of the chamber;
 wherein the device comprises means for reducing the flow speed of the fluid substance at least in the vicinity of the imaging area.

2. The device according to claim 1, further comprising a processing unit capable of determining a value for said solid matter or said fluid substance based at least in part on the captured imagery, said value being a relative or indicative tendency to form deposits value, the total number of imaged particles, number of sticking particles on a surface during a measurement, an averaged number of particles averaged over a predefined surface area, an averaged number of particles averaged over a time period/number of images, a percentage of a covered surface area, size of sticking particles, number of sticking particles in certain size groups, an area of a measurement surface covered by sticking particles, grayscale shade of the imaged particles, color of the imaged particles, or any combination thereof.

3. The device according to claim 2, wherein said processing unit comprises computer readable instructions stored on a non-transitory computer readable medium for instructing a processor to analyze image data from the imaging device.

4. The device according to claim 2, wherein determining a tendency to form deposits or tackiness value for the fluid substance is based on determining at least a number of particles from the fluid substance.

5. The device according to claim 1, wherein the particles sticking to the inner surface are tacky and optionally include one or more of the following:
 recycled fiber stickies,
 wood pitch, and
 coating adhesives.

6. The device according to claim 1, wherein the transparent portion of the chamber is a material selected from the group of plastic, acrylics, polycarbonates and glasses, preferably having a thickness sufficient for the imaging device to focus on particles adhered to the inner surface of the transparent portion.

7. The device according to claim 1, further comprising one or more lighting elements located within or on the transparent portion of the chamber.

8. The device according to claim 1, wherein one or more entire sides of the chamber is made of an at least partially transparent material.

9. The device according to claim 1, further comprising a cleaning means capable of removing particles adhered to said inner surface of the transparent portion of the chamber.

10. The device according to claim 1, wherein the imaging device is arranged to capture images of between a distance of 0-150 µm from the transparent surface.

11. A system for determining a tendency to form deposits of a fluid substance containing solid matter, which is not treated with a dye, the system comprising:
 a chamber having a cavity and at least one transparent or partially transparent portion forming a part of the inner and outer surfaces of said chamber,
 a conduit for a fluid substance stream to be measured, said conduit leading to the cavity of said chamber,
 at least one outlet from the chamber for the substance stream,
 an imaging device arranged to capture imagery of a space within the cavity or at least a portion of the inner surface of the transparent portion of the chamber, when the fluid substance is flowing through the chamber to expose said inner surface to the fluid substance in the cavity of the chamber, and
 a processing unit for determining a tendency to form deposits value of the solid matter particles contained in said fluid substance based at least in part on image data captured by the imaging device of said particles sticking to said inner surface of the transparent portion of the chamber;
 wherein the system comprises means for reducing the flow speed of the fluid substance at least in the vicinity of the imaging area.

12. The system according to claim 11, wherein the conduit and outlet from the chamber are sin line with each and parallel to said transparent portion of the chamber.

13. The system according to claim 12, wherein the processing unit contains computer readable programming stored on a non-transitory computer readable medium for causing a processor to determine one or more relative tendency to form deposits or tackiness values for the substance over a period of time.

14. The system according to claim 11, wherein the conduit is arranged opposite to said transparent portion of the chamber.

15. The system according to claim 14, wherein the system comprises means to create a stagnation zone for reducing the flow speed of the fluid substance against said surface of the transparent portion of the chamber and the imaging device is arranged to be focused and capture imagery through said transparent portion.

16. The system according to claim 11, further comprising a flushing means capable of removing particles adhered to said inner surface of the transparent portion of the chamber.

17. The system according to claim 11, further comprising one or more lighting elements.

18. A method for measuring the tendency to form deposits of particles present in a fluid substance, which is not treated with a dye, said method comprising the steps of:
 having at least a portion of a fluid substance stream directly originating from a process stream to contact a surface of a transparent portion forming a part of the inner and outer surfaces of a chamber and facing the cavity of the chamber,
 having an imaging device arranged to capture imagery of particles sticking on an exposed inner surface of said transparent portion of the chamber contacted by the substance stream when the substance stream is flowing through the chamber to expose said inner surface to the substance stream,
 capturing one or more images of particles sticking to said inner surface of the transparent portion of the chamber when the substance stream is flowing through the chamber to expose said inner surface to the substance stream,
 analyzing said one or more images to determine the tendency to form deposits of said particles;
 wherein the method comprises reducing the flow speed of the fluid substance at least in the vicinity of the imaging area.

19. The method according to claim 18, wherein the total number of imaged particles, number of sticking particles on a surface during a measurement, an averaged number of particles averaged over a predefined surface area or time period/number of images, a percentage of a covered surface area, size of sticking particles, number of sticking particles in certain size groups, an area of a measurement surface covered by sticking particles, grayscale shade of the imaged particles, color of the imaged particles, or any combination thereof.

20. The method according to claim 18, wherein capturing the one or more images is effected through a transparent portion of the chamber.

21. The method according to claim 18, wherein at least a portion of a substance stream directly originating from a process stream contact a surface of a transparent portion of a chamber facing the cavity of the chamber for a first period of time and also the capturing the one or more images occurs during a second period of time, said second period of time differing from said first period of time.

22. The method according to claim 18, wherein at least a portion of a substance stream directly originating from a process stream contact a surface of a transparent portion of a chamber facing the cavity of the chamber for a first period of time and also the capturing the one or more images occurs during a second period of time, said second period of time overlapping said first period of time.

23. The method according to claim 18, wherein only stationary particles are detected and analyzed and moving particles are neglected.

24. The method according to claim 21, wherein said second period of time is between 2 seconds to 2 hours, more particularly between 1 minute to 30 minutes.

25. The method according to claim 18, wherein at least a portion of the substance stream is diluted prior to contacting said transparent portion of the chamber.

26. The method according to claim 18, said measuring is with a device comprising:
   a chamber having a cavity, said chamber having at least one transparent portion,
   at least one inlet to the chamber for a fluid substance and at least one outlet from the chamber for a fluid substance, and an imaging device arranged to capture imagery of at least a portion of a surface of the transparent portion of the chamber or of a space in the vicinity thereof, said surface being exposed to the fluid substance in the cavity of the chamber, wherein
   said imaging device is adapted to produce image data representative of the tendency to form deposits of the fluid substance containing solid matter particles sticking to said surface of the transparent portion of the chamber.

27. The method according to claim 18, wherein at least a portion of the flow of the substance is arranged to be <0.1 m/s, or more preferably <0.03 m/s, at the transparent portion.

28. The method according to claim 18, wherein the particles sticking to the inner surface are tacky and optionally include one or more of the following: recycled fiber stickies, wood pitch or adhesives originating from coated broke.

29. The method according to claim 18 for controlling chemical dosage into a process, wherein the chemical is capable of modifying the tendency to form deposits of solid matter present in a fluid substance in said process.

30. The method according to claim 29, wherein the chemical is a passivation agent, dispersing agent, surfactant or fixative, or a combination thereof.

31. The method according to claim 29, wherein said fluid comprises recycled fibers or mechanical pulp or coated broke.

32. The method according to claim 29, wherein the sensor is located in or analysed fluid is originating from recycled fiber processing line or paper, board or tissue machine process before web formation, in particular in approach system flows having thin stock (<3% consistency).

* * * * *